(12) United States Patent
Craven

(10) Patent No.: US 7,342,100 B2
(45) Date of Patent: Mar. 11, 2008

(54) HPR6 MUTANTS AND USES THEREOF

(75) Inventor: Rolf Joseph Craven, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 142 days.

(21) Appl. No.: 10/860,649

(22) Filed: Jun. 4, 2004

(65) Prior Publication Data

US 2005/0272045 A1   Dec. 8, 2005

(51) Int. Cl.
*C07K 14/00* (2006.01)
(52) U.S. Cl. ..................................... 530/350
(58) Field of Classification Search ................ 530/350
See application file for complete search history.

(56) References Cited

OTHER PUBLICATIONS

Hand et al (J of Cellular Biochemistry, 2003, 90:534-547).*
Hand, Randal A., et al. "*Saccharomyces cerevisiae* Dap1p, a Novel DNA Damage Response Protein Related to the Mammalian Membrane-Associated Progesterone Receptor" Eukaryotic Cell, American Society for Microbiology, Apr. 2003, vol. 2, pp. 306-317, <http://ec.asm.org/cgl/content/full/2/2/306>.

* cited by examiner

*Primary Examiner*—Susan Ungar
*Assistant Examiner*—Laura B Goddard
(74) *Attorney, Agent, or Firm*—McDermott Will & Emery LLP

(57) ABSTRACT

Methods and agents that interfere with Hpr6 function in non-sarcoma tumor cells are disclosed. Anti-Hpr6 agents are used to enhance the killing effect of anti-cancer agents in non-sarcoma tumor cells and to teat non-sarcoma tumors.

1 Claim, 7 Drawing Sheets

A.

Ad-LacZ  Ad-Hpr6-mut

B.

Ad-LacZ  Ad-Hpr6-mut

A.

B.

| bright | fluor | |
|---|---|---|
|  |  | Vector: pBK-CMV |
|  |  | Vector: pBK-HPR6 |
|  |  | Vector: pBK-HPR6 |

FIGURE 7

```
1   ATGGCTGCCGAGGATGTGGTGGCGACTGGCGCCGACCCAAGCG
1    M  A  A  E  D  V  V  A  T  G  A  D  P  S  D

43  ATCTGGAGAGCGGCGGGCTGCTGCATGAGATTTTCACGTCGCC
16     L  E  S  G  G  L  L  H  E  I  F  T  S  P
                                              --
85  GCTCAACCTGCTGCTGCTTGGCCTCTGCATCTTCCTGCTCTAC
30     L  N  L  L  L  L  G  L  C  I  F  L  L  Y

127 AAGATCGTGCGCGGGGACCAGCCGCCGGCCAGCGGCGACAGCG
44   K  I  V  R  G  D  Q  P  A  A  S  G  D  S  D

169 ACGACGACGAGCCGCCCCCTCTGCCCCGCCTCAAGCGGCGCGAC
59     D  D  E  P  P  P  L  P  R  L  K  R  R  D

211 TTCACCCCCGCCGAGCTGCGGCGCTTCGACGGCGTCCAGGACCC
73    F  T  P  A  E  L  R  R  F  D  G  V  Q  D  P

253 GCGCATACTCATGGCCATCAACGGCAAGGTGTTCGATGTGACCA
88     R  I  L  M  A  I  N  G  K  V  F  D  V  T  K

295 AAGGCCGCAAATTCTACGGGCCCGAGGGGCCGTATGGGGTCTTT
103    G  R  K  F  Y  G  P  E  G  P  Y  G  V  F

337 GCTGGAAGAGATGCATCCAGGGGCCTTGCCACATTTTGCCTGGA
117 A  G  R  D  A  S  R  G  L  A  T  F  C  L  D

379 TAAGGAAGCACTGAAGGATGAGTACGATGACCTTTCTGACCTCA
132  K  E  A  L  K  D  E  Y  D  D  L  S  D  L  T

421 CTGCTGCCCAGCAGGAGACTCTGAGTGACTGGGAGTCTCAGTTC
147    A  A  Q  Q  E  T  L  S  D  W  E  S  Q  F

463 ACTTTCAAGTATCATCACGTGGGCAAACTGCTGAAGGAGGGGGA
161 T  F  K  Y  H  H  V  G  K  L  L  K  E  G  E

505 GGAGCCCACTGTGTACTCAGATGAGGAAGAACCAAAAGATGAGA
176   E  P  T  V  Y  S  D  E  E  E  P  K  D  E  S

547 GTGCCCGGAAAAATGATTAAAGCATTCAGTGGAAGTATATCTAT
191    A  R  K  N  D  *

591 TTTTGTA
```

HPR6 MUTANTS AND USES THEREOF

FIELD OF THE INVENTION

The invention relates to Hpr6 mutants and their use. In particular, the present invention relates to the use of the human Hpr6 protein as a target for development of anti-cancer drugs, as well as adenoviral vectors encoding a mutant Hpr6 for use in anti-cancer therapy.

BACKGROUND OF THE INVENTION

Therapeutic treatments for solid tumors usually include a combination of DNA damaging agents, including a class of compounds that are metabolized by the CYP3A4 protein. These DNA damaging agents include topoisomerase inhibitors, and doxorubicin or adriamycin, which is an anthracycline antibiotic that is frequently used in combination with other drugs for treating breast cancer. Doxorubicin acts through multiple mechanisms that include intercalating within DNA, binding to topoisomerase II, and generating reactive oxygen species. The effectiveness of doxorubicin- or topoisomerase inhibitor-based chemotherapy is limited by drug resistance. For example, doxorubicin resistance can emerge through alterations of proteins regulating the availability, activation, or inactivation of the drug, through changes in topoisomerase II, or through changes in pathways mediating DNA repair and apoptosis. The proteins that cause chemotherapeutic resistance are potential therapeutic targets for cancer, and inhibiting these proteins could lead to improved effectiveness of doxorubicin and other compounds that are metabolized by Cyp3A4.

Hpr6 is a member of the heme-1 domain family of proteins, which includes the human Hpr6 and Dg6 proteins, the rodent 25-Dx and IZAg proteins, and the budding yeast Dap1p protein. The Hpr6/25-Dx/IZAg/Dap1p proteins are relatively small (approximately 25 kDa) and are composed largely of a central heme-1 domain that shares homology with cytochrome $b_5$. Like cytochrome $b_5$, the IZAg protein binds to heme. Dap 1 p damage resistance protein, 7) was previously identified in *Saccharomyces cerevisiae*, a model organism for studying chemotherapeutic resistance. Yeast mutants lacking Dap 1 p exhibit extreme sensitivity to a DNA alkylating agent and are moderately sensitive to hydroxyurea and radiation (Hand R A et al., *Eukaryotic Cell* 2003; 2: 121-32).

Thus, drugs that target the Hpr6 protein are potentially useful for treating cancer. Drug resistance is one of the primary causes underlying failure of treatment for cancer, and there is a profound need to screen for inhibitors of the Hpr6 pathway.

SUMMARY OF THE INVENTION

In one aspect of the invention there is provided a mutant Hpr6 polypeptide (Hpr6-mut) consisting of the amino acid sequence SEQ ID NO:1.

In another aspect of the invention there is provided an isolated nucleic acid encoding Hpr6-mut.

In another aspect of the invention there is provided a vector encoding Hpr6-mut. In preferred embodiments, the vector is an adenoviral vector, most preferably a replication deficient adenoviral vector; or a plasmid.

In a further aspect of the invention there is provided a method for treating a non-sarcoma tumor comprising administering to a patient an anti-cancer agent that is metabolized by Cyp3A4 and a replication defective adenovirus vector comprising a nucleotide sequence encoding Hpr6-mut, wherein the Hpr6-mut is expressed in said tumor. In a preferred embodiment the anti-cancer agent is doxorubicin.

In another aspect of the invention there is provided a method of enhancing the effect of a Cyp3A4 metabolizable anti-cancer agent in a non-sarcoma tumor of a patient comprising administering to the patient a replication defective adenovirus vector comprising a nucleotide sequence encoding Hpr6-mut; and administering the Cyp3A4 metabolizable anti-cancer agent to the patient, wherein the Hpr6-mut is expressed in said tumor. In a preferred embodiment the anti-cancer therapeutic agent is administered within about one to about twenty four hours of administration of the adenoviral vector.

In another aspect of the invention there is a method of screening test agents comprising contacting cells that overexpress Hpr6 with the test agents and doxorubicin or other Cyp3A4 metabolizable anti-cancer agent; wherein test agents that result in enhanced cell death compared to Hpr6 overexpressing cells that are contacted with only the Cyp3A4 metabolizable anti-cancer agent are identified as anti-Hpr6 agents.

BRIEF DESCRIPTION OF THE DRAWINGS

FIG. 7. The amino acid sequence (SEQ ID NO:1) and corresponding nucleotide sequence (SEQ ID NO:2) of Hpr6-mut are shown. The heme binding region (SEQ ID NO:3) is highlighted by underlining. In Hpr6-mut, the aspartic acid (D) at amino acid position 120 within the heme binding region is mutated to glycine (G), which inactivates the protein (SEQ ID NO:11).

DETAILED DESCRIPTION OF THE INVENTION

Figure 1:
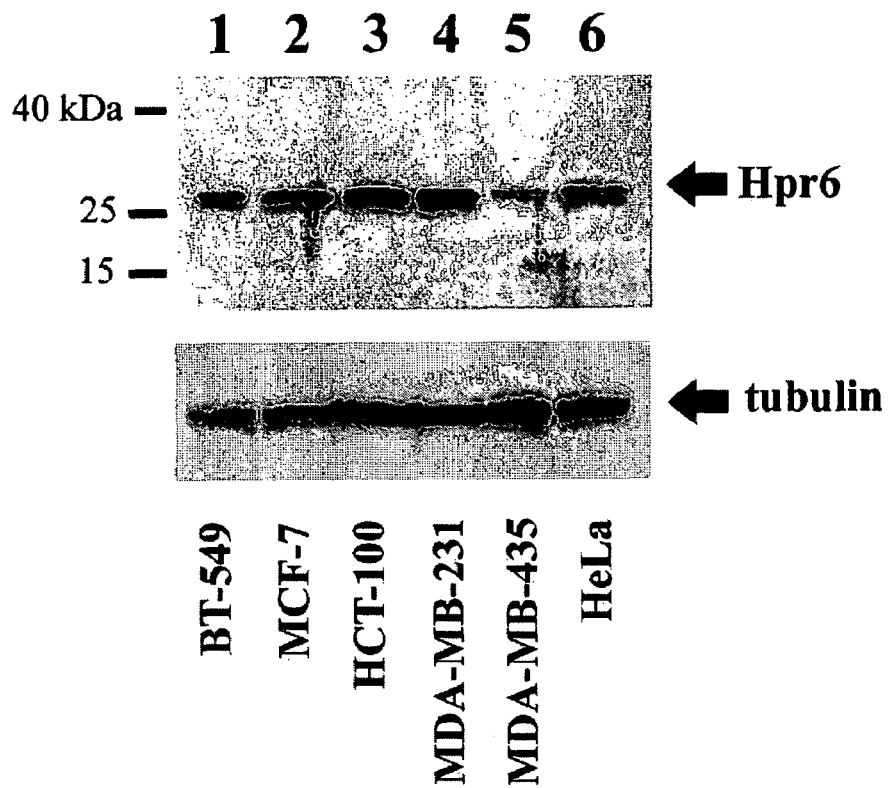
FIG. 1 shows that Hpr6 is expressed in breast cancer cell lines and is induced by doxorubicin. 1A: western blot analysis showing expression of Hpr6 (top panel) and tubulin (bottom panel) in the cell lines BT549 (lane 1), MCF-7 (lane 2), HCT-100 (lane 3), MDA-MB-231 (lane 4), MDA-MB-435 (lane 5), and HeLa (lane 6). Hpr6 migrates as a 27 kDa protein. The position of molecular weight markers is indicated to the left. 1B: Hpr 6 expression is induced after treatment with doxorubicin and camptothecin. MDA-MB-231 cells were untreated (upper panel, lane 1), treated with 0.5 or μM doxorubicin (upper panel, lanes 2 and 3), or 0.25 1 μm camptothecin (upper panel, lane 4) for 3 days, and the expression of Hpr6 was analyzed by western blot. Hpr6 expression was elevated sharply by exposure to the two drugs as indicated by the fold increase indicated below the upper panel. Tubulin is included as a control for equal protein loading (lower panel).
Figure 1:
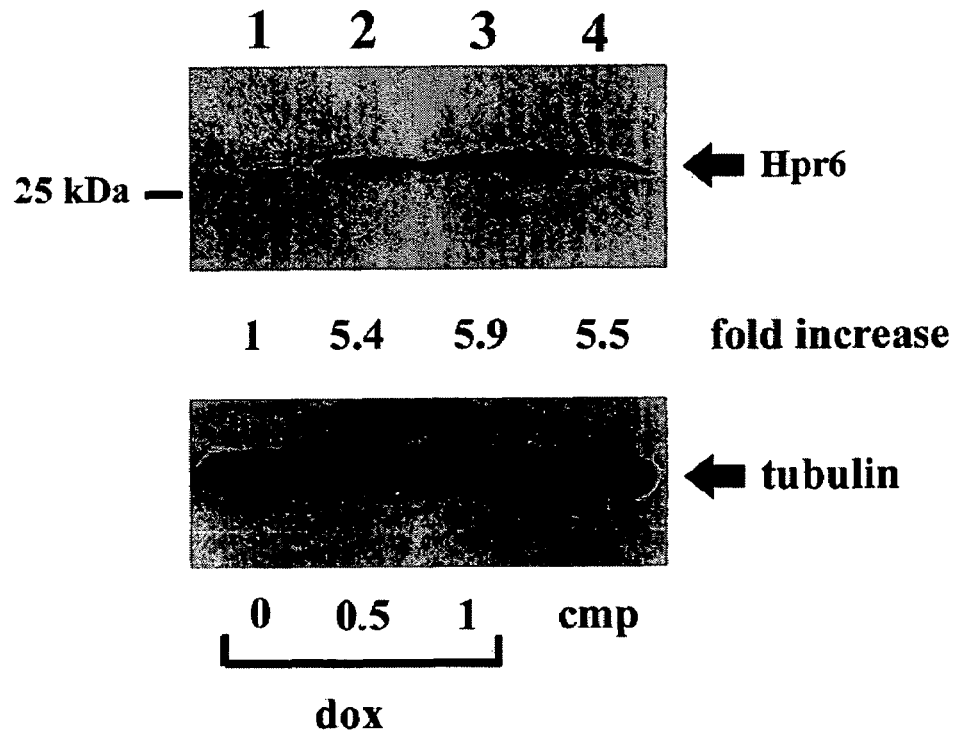

The Hpr6 protein (also referred to as Hpr6.6, MAPR, and PGRMC-1) is a heme1 domain protein that is believed to regulate the turnover of cellular metabolites. It is shown herein that Hpr6 is overexpressed in cancer cells, such as human breast, colon and thyroid tumors (but not in sarcomas), and tumor-derived cell lines and functions therein to protect these cells from cell death.

The Hpr6-related proteins are proposed to play a role in metabolism and cancer for the following reasons: (a) the rat 25-Dx protein and its porcine homologues are microsomal proteins that bind to progesterone and regulate its metabolism; (b) the rat 25-Dx protein is up-regulated in liver tumors induced by dioxin; and (c) breast cancer cells engineered to overexpress Hpr6 are hypersensitive to oxidative damage (Hand R A and Craven R J. Journal of Cellular Biochemistry 2003; 90: 534-47). However, fundamental questions such as the localization of Hpr6, its expression in cancer, and its biochemical activities have not been previously reported.

To test the role of Hpr6 in resistance to chemotherapeutic agents, an efficient means of inhibiting Hpr6 in tumors was developed, and the ability of cells with inhibited Hpr6 function to respond to damage was tested. Breast cancer cells were infected with an adenovirus bearing a dominant-negative mutant of Hpr6 and treated with doxorubicin and other anti-cancer agents. It is shown herein that expression of mutant Hpr6 triggers cell death following anti-cancer agent therapy, such as for example doxorubicin therapy or other anti-cancer agents that are metabolized by Cyp3A4. This suggests that Hpr6 might function in tumors to promote chemotherapeutic resistance. It is also shown that Hpr6 is overexpressed in approximately half of clinical breast tumor samples. Together, these findings indicate that Hpr6 mediates resistance to chemotherapeutic agents in cancer cells and is a target for therapeutic intervention.

The studies disclosed herein demonstrate that; (i) Hpr6 is overexpressed in breast tumors; and (ii) Hpr6 binds to heme and localizes to the endoplasmic reticulum; and (iii) an inactive mutant of the Hpr6 protein which inhibits Hpr6 heme binding sensitizes metastatic cancer cells to chemotherapeutic agents, in particular Cyp3A4 metabolizable compounds. The role of Hpr6 in cancer has not been examined previously, and these results demonstrate that Hpr6 function in normal cells is corrupted in tumors cells to yield improved resistance to chemotherapeutic agents, e.g., etoposide (ETP), adriamycin (doxorubicin: DOX), taxol, paclitaxol and irinotecan (CPT-11) and other Cyp3A4 metabolizable anti-cancer agents for example.

There is a precedent for Hpr6 homologues directing resistance to DNA damaging agents, because the Hpr6 yeast homologue is required for resistance to the methylating agent MMS and plays a minor role in resistance to radiation (Hand R A et al. Eukaryotic Cell 2003; 2: 121-32). There is also a precedent for Hpr6 homologues regulating metabolism, because the rodent Hpr6 homologue increases hydroxylation of progesterone, a key step in its metabolism (Min L et al. Mol Cell Endocrin 2004; 215: 143-8). Our results suggest that the effects of Hpr6 on xenobiotic compounds are fairly specific to compounds that are metabolized by Cyp3A4. A mutant of Hpr6, referred to herein as Hpr6-mut, inhibited survival following doxorubicin treatment, but had no effect on survival from treatment with mechlorethamine. This was somewhat surprising given that yeast lacking the Hpr6 homologue, Dap1p, are extremely sensitive to alkylating agent MMS (Hand R A et al. Eukaryotic Cell 2003; 2: 121-32), but are relatively insensitive to doxorubicin (Craven, unpublished observations). Thus, it appears that the specificities of Dap1p and Hpr6 differ, perhaps due to species differences.

Hpr6 expression is induced by doxorubicin and camptothecin, and Hpr6 induction parallels the activity of the Ad-Hpr6-mut adenovirus to various drugs, including doxorubicin, camptothecin and etoposide, for example. Microarray analyses have identified a number of proteins that are induced by doxorubicin, including the DNA repair gene XRCCl, the Fms-related tyrosine kinase, and the 268 proteosome regulatory sub-unit 4 (Kudoh et al. Cancer Res 2000; 60: 4161-4166) A similar analysis in patients treated with doxorubicin revealed similar changes in DNA repair genes, protein kinases, members of the proteosome pathway (Sotiriou et al. *Breast Cancer Res* 2002; 4: R3-11), although the specific genes differed from those identified previously. Hpr6 (sometimes listed in databases as "PGRMC1" for progesterone receptor membrane component 1) was not present on early microarrays, perhaps due to the high G-C content in the 5' region of the gene. Our results suggest that Hpr6 is induced as a part of a global response to neutralize topoisomerase inhibitor chemotherapeutic agents such as doxorubicin or resist cell death. It is shown herein, however, that overexpression of the Hpr6-mut protein overcomes this response.

The role for Hpr6 in providing resistance to Cyp3A4 metabolizable anti-cancer agents is consistent with its localization to the perinuclear region, which is also the site for numerous cytochrome P450 proteins and drug metabolizing proteins (Rieger et al. *Cancer Res* 2004; 64: 2357-64). In addition, doxorubicin accumulates in the perinuclear region in drug-resistant cell lines (Rajagopal et al. *Mol Bioi Cel/* 2003; 14: 3389-99), presumably sequestering the drug from its nuclear site of action. Interestingly, cytochrome $b_5$, the prototype heme-1 domain protein and a relative of Hpr6, localizes to the endoplasmic reticulum (D'Arrigo et al. *J Bioi Chern* 1993; 268: 2802-8) as does the heme metabolizing protein heme oxygenase (Volti et al. *Biochem and Biophys Res Comm* 2004 315: 517-524). The perinuclear staining pattern for Hpr6 resembles that reported for rodent homologues of Hpr6 in liver, while Hpr6 homologues have an additional membrane component in neuronal cells.

Our results suggest that Hpr6 resides in the endoplasmic reticulum, where it binds to heme and regulates resistance to anti-cancer agents. It is proposed that Hpr6 up-regulates the activity of proteins that metabolize chemotherapeutic agents such as doxorubicin, which includes CYP3A4 or aldoketoreductase and that Hpr6-mut blocks this function. There is a precedent for Hpr6 homologues acting to promote CYP protein function. The rodent Hpr6 homologue, IZAg, increases CYP activity for 21-hydroxylation of progesterone. Furthermore, the yeast Dap1p protein targets the protein Cyp51 (also known as Ergl1p), a highly conserved P450 protein. Alternately, Hpr6 could regulate the activity of an aldoketoreductase (Peltoketo et al. *J Mol Endocrin* 1999; 23: 1-11) which reduces a ketone group at the C-13 position of doxorubicin. Through either mechanism, Hpr6 would ultimately drive the metabolism of therapeutic agents such as doxorubicin, and disruption of Hpr6 function with the Hpr6-mut protein would lead to cell death.

Figure 2:
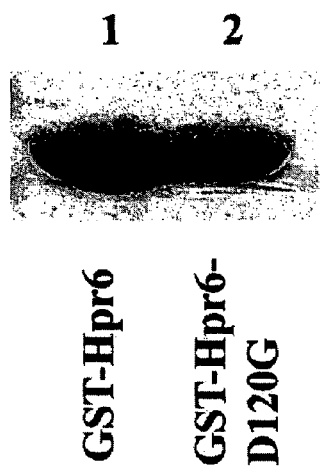
FIG. 2. The Ad-Hpr6-mut adenovirus directs expression of an inactive form of Hpr6. 2A: Purification of GST-Hpr6 (lane 1) and GST-Hpr6-mut (lane 2) fusion proteins. Proteins were purified using glutathione-agarose and analyzed by SDS-PAGE electrophoresis. 2B: Heme binding by Hpr6 (left column) but not Hpr6-mut (right column). Solubilized proteins were analyzed for absorbance at 400 nm, and measurements were performed in triplicate. 2C: western blot analysis of MDA-MB-231 cells infected with 500, 1000, or 2000 pfu/cell of Ad-Hpr6-mut (lanes 1-3) or 2000 pfu/cell of Ad-LacZ (lane 4). Hpr6 expression was visualized with an antibody to the HA epitope tag. D. The Hpr6-mut protein is overexpressed compared to endogenous Hpr6 following Ad-Hpr6-mut infection. MDA-MB 231 cells were infected with Ad-LacZ (lane 1) or Ad-Hpr6-mut (lane 2) and analyzed by western blots probed for HA (top panel), Hpr6 (middle panel), or tubulin (bottom panel). The positions of the exogenous Hpr6-mut and endogenous Hpr6 protein are indicated in the center panel (top and bottom, respectively).
Figure 2:
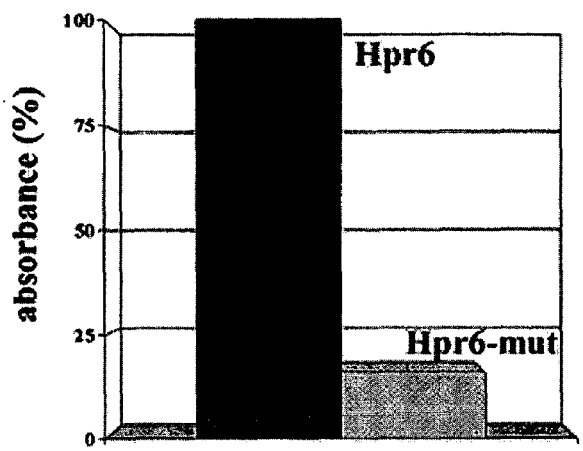
Figure 2:
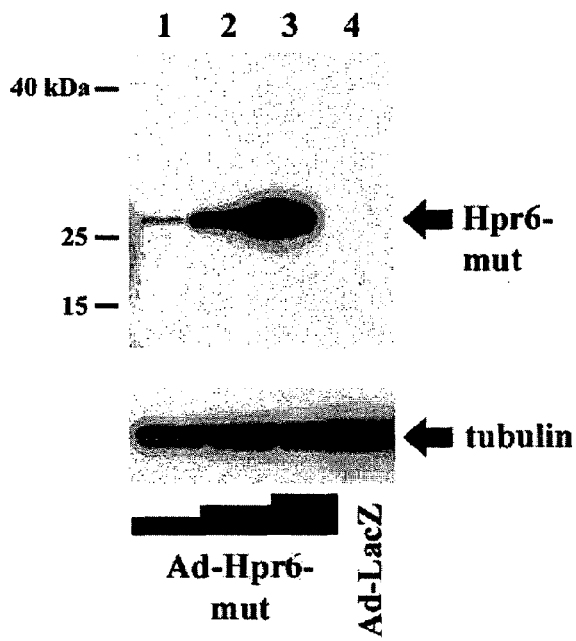
Figure 2:
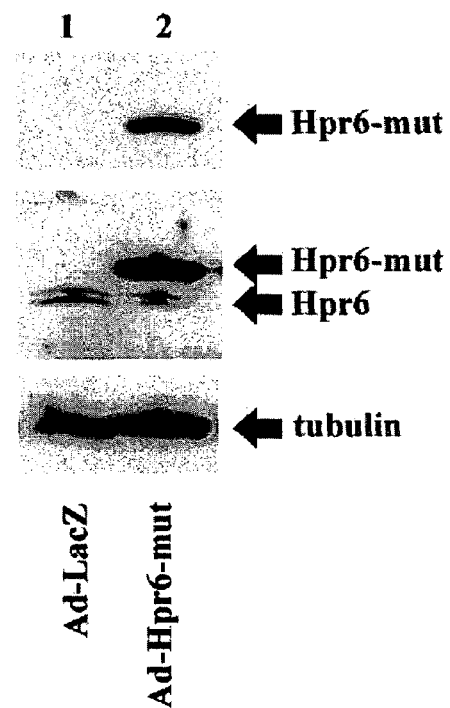

The structural basis through which Hpr6-mut disrupts Hpr6 function is unknown. One likely mechanism for Hpr6-mut is competition with endogenous Hpr6 for binding to substrates and associated proteins. However, there is evidence that Hpr6 homologues function as a covalently bound dimer. Thus, Hpr6-mut could bind directly to wild-type Hpr6, forming an inactive complex. Inactive homodimer formation is a common mechanism among dominant-negative mutants (Rishi et al. *J Bioi Chern* 2004; 279: 11863-74; and Zhu et al. *Mol Cell Bioi* 2004; 24: 2673-81), including drug resistance proteins (Kage et al. *J Cancer* 2002; 97: 626-30) and cytochrome proteins (Curry et al. *Genomics* 2004; 83: 425-38). However, covalently bound dimers between endogenous Hpr6 and Hpr6-mut would have been detected on western blots of infected cells (such as those in FIG. 2), and these bands were not observed.

Thus, Hpr6 appears to function in protecting tumor cells from anti-cancer agents that are metabolizable by Cyp3A4. In normal tissues, Hpr6 is highly expressed in liver and kidney (Gerdes et al. *Biol Chem* 1998; 379: 907-11), tissues that are directly exposed to compounds taken up by the digestive tract and which express proteins that neutralize these compounds, such as P450 proteins (Watkins et al. *Proc Natl Acad Sci* 1985; 82: 6310-4; and Phillips et al. *Proc Natl Acad Sci* 1985; 82: 983-987).

When overexpressed in non-sarcoma tumors, such as breast tumor, lung tumors, ovarian tumors, colon tumors or thyroid tumors, for example, Hpr6 protects tumor cells from Cyp3A4 matabolizable compounds, such as doxorubicin, etoposide and camptothecin providing resistance to this class of chemotherapeutic drugs. Furthermore, inhibiting Hpr6 increases the ability of chemotherapeutic drugs to kill cancer cells, which makes Hpr6 a target for intervention in cancer therapy.

Hpr6 is overexpressed in colon and thyroid tumors (but not in sarcomas), as well as breast tumors. It has also been demonstrated that Hpr6 levels are elevated in lung cancer tumor cells (Difilippantonio, et al., Eur. Journal of Cancer 39: 1936, 2003) and some unpublished data from a microarray analysis show that it is elevated in ovarian cancer (L. Miller and E. T. Liu, personal communication). Thus, Hpr6 is widely overexpressed in non-sarcoma cancer cells.

Thus, Hpr6 is an excellent target for screening agents that enhance the effect of anti-cancer agents. In a typical assay for compounds or agents that inhibit Hpr6 activity, cells that overexpress Hpr6 are exposed to the test agent or compound and doxorubicin or other Cyp3A4 metabolizable anti-cancer agent; and test agents or compounds that result in enhanced cell death compared to cells that are exposed only to the Cyp3A4 metabolizable anti-cancer agent are identified as anti-cancer agents. The test compound may be a small molecule, peptide, peptoid, monoclonal or polyclonal antibody or fragment thereof, an RNA/DNA aptamer, siRNA or anti-sense nucleic acid that binds to Hpr6 nucleic acid and inactivates it, or the like.

It is well known in the art that viability of a cell can be determined by contacting the cell with a dye and viewing it under a microscope. Viable cells can be observed to have an intact membrane and do not stain, whereas dying or dead cells having "leaky" membranes do stain. Incorporation of the dye by the cell indicates the death of the cell. The most common dye used in the art for determining viability is trypan blue. Viability of cells can also be determined by detecting DNA synthesis. Cells can be cultured in cell medium with labeled nucleotides (e.g., $^3$H thymidine). The uptake or incorporation of the labeled nucleotides indicates DNA synthesis and cell viability. In addition, colonies formed by cells cultured in medium indicate cell growth and is another means to test viability of the cells.

Identification and/or observation of cells undergoing apoptosis can be another method of determining cell viability. Apoptosis is a specific mode of cell death recognized by a characteristic pattern of morphological, biochemical, and molecular changes. Cells going through apoptosis appear shrunken, and rounded; they also can be observed to become detached from culture dish. Thermophological changes involve a characteristic pattern of condensation of chromatin and cytoplasm which can be readily identified by microscopy. When stained with a DNA-binding dye, such as H33258, apoptotic cells display classic condensed and punctate nuclei instead of homogeneous and round nuclei.

The hallmark of apoptosis is the endonucleolysis, a molecular change in which nuclear DNA is initially degraded at the linker sections of nucleosomes to give rise to fragments equivalent to single and multiple nucleosomes.

When these DNA fragments are subjected to gel electrophoresis, they reveal a series of DNA bands which are positioned approximately equally distant from each other on the gel. The size difference between the two bands next to each other is about the length of one nucleosome (i.e., 20 base pairs). This characteristic display of the DNA bands is called a DNA ladder and it indicates apoptosis of the cell. Apoptotic cells can be identified by flow cytometric methods based on measurement of cellular DNA content, increased sensitivity of DNA to denaturation, or altered light scattering properties. These methods are well known in the art and are within the contemplation of the invention.

As used herein, "compound" refers to any agent, chemical substance, or substrate, whether organic or inorganic, or any protein including antibodies and functional fragments thereof, peptides, polypeptides, peptoids, and the like.

Agents that inactivate Hpr6 also include mutants of Hpr6 that interfere with wild-type Hpr6 activity when administered to cells. For example, Hpr6-mut, and other mutants of Hpr6 that cannot bind heme are useful anti-cancer agents. Such mutants include those that have mutations, such as point mutations, deletions or additions, for example, to the heme binding site of the protein, which is shown in FIG. 7.

As used herein, the term "antibody" refers to an immunoglobulin molecule with a specific amino acid sequence evoked by an antigen, e.g. Hpr6 or the heme binding region of Hpr6, and characterized by reacting specifically with the antigen in some demonstrable way. The term "antibody" encompasses polyclonal and monoclonal antibody preparations, CDR-grafted antibody preparations, as well as preparations including hybrid antibodies, altered antibodies, F(AB)'.sub.2 fragments, F(AB) molecules, Fv fragments, single domain antibodies, chimeric antibodies and functional fragments thereof which exhibit immunological binding properties of the parent antibody molecule. The antibodies can also be humanized.

The term "monoclonal antibody" is not limited to antibodies produced through hybridoma technology. The term "monoclonal antibody" refers to an antibody or functional fragment thereof that is derived from a single clone, including any eukaryotic, prokaryotic, or phage clone, and not the method by which it is produced.

Test agents that are identified as anti-cancer agents (referred to herein as anti-Hpr6 agents) can be used to treat non-sarcoma tumors. Therapeutic treatment of non-sarcoma tumors comprises administration of an effective amount of the anti-Hpr-6 agent and a Cyp3A4 metabolizable anti-cancer agent to a patient. In a preferred embodiment, the anti-cancer agent is doxorubicin, although other Cyp3A4 metabolizable anti-cancer agents or combinations of agents may be used. In one embodiment of this aspect of the invention the anti-Hpr6 agent is a mutant form of the Hrp6 gene, such as Hprt6-mut, which interferes with the ability of wild-type Hpr6 to protect cells from the effects of Cyp3A4 matabolizable anti-cancer agents. The skilled practitioner can determine the effective amount of anti-Hpr6 agent required to induce such interference.

The anti-Hpr6 agent and anti-cancer agent may be administered simultaneously, or within a short time of one another, e.g., about one to 24 hours. In the latter case it is preferred that the anti-Hpr6 agent is administered first, but the order of administration is not essential. Preferably, the anti-Hpr6 agent is administered by direct injection into a tumor to be treated. However, systemic administration is also possible.

The present invention also provides a vector, preferably a plasmid or an adenoviral vector, which encodes Hpr6-mut or other mutant of Hpr6 that enhances the sensitivity of a tumor cell that overexpresses Hpr6 to Cyp3A4 metabolizable drugs when expressed therein. In a most preferred embodiment, the vector is a replication-deficient adenoviral vector. The vector may encode, for example, a mutant of Hpr6 that has a mutation in the heme binding region of the gene or a fragment of Hrp6 that interferes with the ability of wild-type Hpr6 to protect cells from the effects of Cyp3A4 matabolizable anti-cancer agents, e.g., etoposide, doxorubicin, taxol, paclitaxol and camptothecin when expressed in the cells.

The present invention also provides kits for the treatment of non-sarcoma tumors comprising at least one Cyp3A4 metabolizable anti-cancer agent and at least one anti-Hpr6 agent. The anti-cancer agent may be for example, doxorubicin, etoposide, camptothecin, and combinations thereof. The anti-Hrp6 agent is any agent or combination of agents that interfere with the ability of wild-type Hpr6 to protect tumor cells from the killing effects of the anti-cancer agent. For example, the anti-Hpr6 agent may be an adenoviral vector, preferably a replication deficient adenoviral vector encoding Hpr6-mut.

The following examples are presented for the illustrative purposes and it is to be understood that the present invention is not limited to those precise embodiments, and that various changes and modifications can be effected therein by one skilled in the art without departing from the scope and spirit of the invention as defined by the appended claims.

EXAMPLE 1

Generation of a Hrp6 Mutant. Hpr6 was cloned in two stages. First, the amino terminal 109 amino acids were amplified from purified MCF-7 cell genomic DNA using the primers HPR1FHA (5'-CCCGGGGGATCCGACGCCGC-CACCATGGAATCCGACTACCCCTATGAT-GTGCCCGATTACGTCGAGTCCGTCGC-CGAGGATGTGGTGGCG-3') (SEQ ID NO:6) and HPR330R (5'-CCCATACGGCCCCTCGGGCC-3') (SEQ ID NO:7). The former primer added a single HA epitope tag sequence (Asp-Tyr-Pro-Tyr-Asp-Val-Pro-Asp-Tyr-Ala-Glu-Ser)(SEQ ID NO:4) to the amino terminus of the Hpr6 open reading frame. The amplified DNA was subcloned into the TA cloning vector pCR2.1 (InVitrogen; Carlsbad, Calif.), then digested with BamHI and KpnI and ligated into the plasmid pBK-CMV (Stratagene, LaJolla, Calif.), forming the plasmid pRC38. A fragment containing the 3' end of Hpr6 was amplified from the plasmid IMAGE 3254089 (Research Genetics; Huntsville, Ala.) using the primers HPR126F (5'-ACAAGATCGTGCGCGGGGA-3') (SEQ ID NO:8) and HPR690R-APA (5'-TGTGGGCCCCTC-GAGAAACTTATAGCAAGTGCTC-3') (SEQ ID NO:9), digested with ApaI, and inserted into the ApaI site of the plasmid pRC38, forming the plasmid pRC40. The integrity of all plasmid insets was verified by automated sequencing.

The 3' end of the HPR6 open reading frame containing the D120G mutation was amplified from the plasmid IMAGE 3254089 (Research Genetics, Huntsville, Ala.) using the primers HPR-D120G-F (5'-TACGGGCCCGAGGGGCCG-TATGGGGTCTTTGCTGGAAGAGATG-CATCCAGGGGCCTTGC-3') (SEQ ID NO:10) and HPR-690R-APA (SEQ ID NO:9). The resulting PCR product was digested with ApaI and cloned into the same site of the plasmid pRC38, which included the 5' end of the HPR6 open reading frame. The resulting plasmid, pRC42, contained the full-length HPR6 open reading frame with the D120G mutation. The HPR6-D120G open reading frame was excised by digestion with BamHI and XhoI and cloned into the BglII and XhoI sites of pShuttle-CMV (provided by the University of North Carolina at Chapel Hill Adenoviral Core Facility), resulting in the plasmid pRC45.

EXAMPLE 2

Expression plasmids and viral preparation. The 3' end of the HPR6 open reading frame containing the DI20G mutation was amplified from the plasmid IMAGE 3254089 (Research Genetics, Huntsville, Ala.) using the primers HPR-DI20G-F and HPR-690R-APA (primer sequences available on request). The resulting PCR product was digested with ApaI and cloned into the same site of the plasmid pRC38 (Hand et al. *Journal of Cellular Biochemistry* 2003; 90: 534-47.), which included the 5' end of the HPR6 open reading frame. The resulting plasmid, pRC42, contained the full-length HPR6 open reading frame with the D 120G mutation. The HPR6-DI20G open reading frame was excised by digestion with BamHI and XhoI and cloned into the BglII and XhoI sites of pShuttle-CMV (provided by the University of North Carolina at Chapel Hill Adenoviral Core Facility), resulting in the plasmid pRC45.

Fusion protein plasmids, preparation, and analysis. Hpr6-GST fusion proteins contained amino acids 43-195 of the Hpr6 open reading frame. Hpr6 was amplified using the primers HPR+126F-Bam and HPR+566R-Xho with the plasmid pRC40 as a template. PCR products were cloned into the pCR2.1 plasmid (InVitrogen, Carlsbad, Calif.) forming the plasmid pRC44. The Hpr6 fragment was then ligated into the Bam HI and Xho I on the plasmid pGEX-4T-I (Amersham Biosciences, Piscataway, N.J.), forming the plasmid pRC46. To introduce the DI20G mutant, the plasmid pRC46 was digested with Apa I and Xho I and ligated to the 260 bp Apa I-Xho I fragment of the plasmid pRC45, forming the plasmid pGC4. The structure of all of these plasmids was verified by automated sequencing.

Fusion protein expression was induced with 1 mM IPTG (Fisher) and cells were lysed in the B-PER reagent (Pierce, Rockford, Ill.) and bound to glutathione-agarose beads (Pierce). At this stage, the GST-Hpr6-bound columns were visibly brown due to bound heme, while the GST-Hpr6-DI20G-bound columns were white due to the inability of this mutant to bind heme. After estimating protein quantity by SDS-PAGE electrophoresis, 100/-1 g of Hpr6 or Hpr6-DI20G proteins were liberated by digestion with I U of thrombin for two hours, and absorbance at 400 nm was determined using a Spectronics Genesys 5 spectrophotometer (Spectronics Instruments, Rochester, N.Y.).

EXAMPLE 3

Hpr6 binds to heme, and the D120G mutation in the heme-1 domain blocks heme-binding activity. Hpr6 is highly conserved with a group of proteins that share the sequence FYGP-x-GPY-x-x FAG-x-DASR-x-LA (SEQ ID NO: 5). An Asp-to-Gly mutation in this sequence inactivates the yeast Dap1p protein (R. Craven, unpublished observations). An analogous D120G mutation was made in Hpr6 and purified the Hpr6 and Hpr6-D120G proteins (FIG. 2A), then tested the proteins for heme binding (FIG. 2B). Hpr6 bound efficiently to heme based on absorbance at 400 nm (FIG. 2B, left column), and this activity was absent in the Hpr6-D120G protein (FIG. 2B, right column). The measurement was performed in triplicate, and the difference between Hpr6 and Hpr6-D120G absorbance was statistically significant (P=0.03). The absorption curve for Hpr6 shifted from 400 nm to 420 nm when the protein was treated with sodium hydrosulfite, as expected (data not shown). We conclude that Hpr6 is a heme-binding protein, and that Hpr6-D120G is an inactive form of the protein.

EXAMPLE 4

The Ad-Hpr6-mut adenovirus efficiently directs expression of Hpr6-D120G. An adenovirus (called Ad-Hpr6-mut) encoding the inactive Hpr6 protein was prepared. MDA-MB-231 human breast cancer cells were infected with the Ad-Hpr6-mut adenovirus, resulting in efficient expression of the Hpr6-mut protein (FIG. 2C, top panel, lanes 1-3). Expression was dependent on the dose of the virus (FIG. 2C, top panel, lanes 1-3), while infection of MDA-MB-231 cells with a control Ad-LacZ adenovirus did not yield any detectable protein expression (FIG. 2C, top panel, lane 4). At a dose of 1000 pfu/cell of Ad-Hpr6-mut, Hpr6-mut was overexpressed relative to the endogenous Hpr6 protein (FIG. 2D, middle panel, indicated as "Hpr6-mut" and "Hpr6", respectively). The identity of the Hpr6-mut protein was confirmed by western blotting with an antibody to the HA epitope tag (FIG. 2D, upper panel, lane 2). We conclude that Hpr6-mut is an inactive form of Hpr6, and that overexpression of Hpr6-mut is capable of acting as a dominant-negative form of the protein.

EXAMPLE 5

Drug treatment, viability assays, and immunological analyses. Doxorubicin (Sigma, St. Louis, Mo.) was added to culture media and incubated for five days. Cells were incubated with hydrogen peroxide (Fisher), mechlorethamine (kindly provided by Dr. Robert Orlowski, University of North Carolina at Chapel Hill) or camptothecin (Sigma) for 72 hours. Trypan blue and MTT assays were performed using standard techniques as previously described (Hand et al. *Journal of Cellular Biochemistry* 2003; 90: 534-47). Western blots of cultured cells and tumors were performed as described previously (Hand et al. *Journal of Cellular Biochemistry* 2003; 90: 534-47; Yang et al. *Tumor Biology* 2003; 24: 61-9). The antibodies used were as follows: anti-HA (HAll, BAbCo, Berkeley, Calif.), tubulin (Fisher), and Hpr6 (Meyer et al. *Steroids* 1998; 63: 111-6). Cells were visualized using a VistaVision inverted microscope attached to a Sony DCS F717 digital camera (VWR, Batavia, Ill.). For immunofluorescence, MCF-7/vector and MCF-7/Hpr6 cells (Hand et al. *Journal of Cellular Biochemistry* 2003; 90: 534-47) were fixed with 3.7% formaldehyde, permeabilized with 0.1% Triton X-100, blocked with 10% normal goat serum, and incubated with the HAll monoclonal antibody. Cells were then washed, incubated with a FITC-labeled anti-mouse secondary antibody (Santa Cruz Biotechnology, Santa Cruz, Calif.), washed, mounted, and visualized using a Zeiss fluorescent microscope.

Ad-Hpr6-mut synergizes with doxorubicin in MDA-MB-231 breast cancer cells. The effect of the Ad-Hpr6-mut adenovirus in response to chemotherapy was analyzed for two reasons. First, the budding yeast homologue of Hpr6 controls resistance to damaging agents. Second, we found that Hpr6 expression is induced in response to the chemotherapeutic drugs doxorubicin and camptothecin in the breast cancer cell line MDA-MB-231 (FIG. 1B), as well as in MCF-7 cells (data not shown). In contrast to these findings, Hpr6 expression was not induced in response to the chemotherapeutic drugs cisplatinum and mechlorethamine or following treatment with hydrogen peroxide (data not shown).

Figure 3:
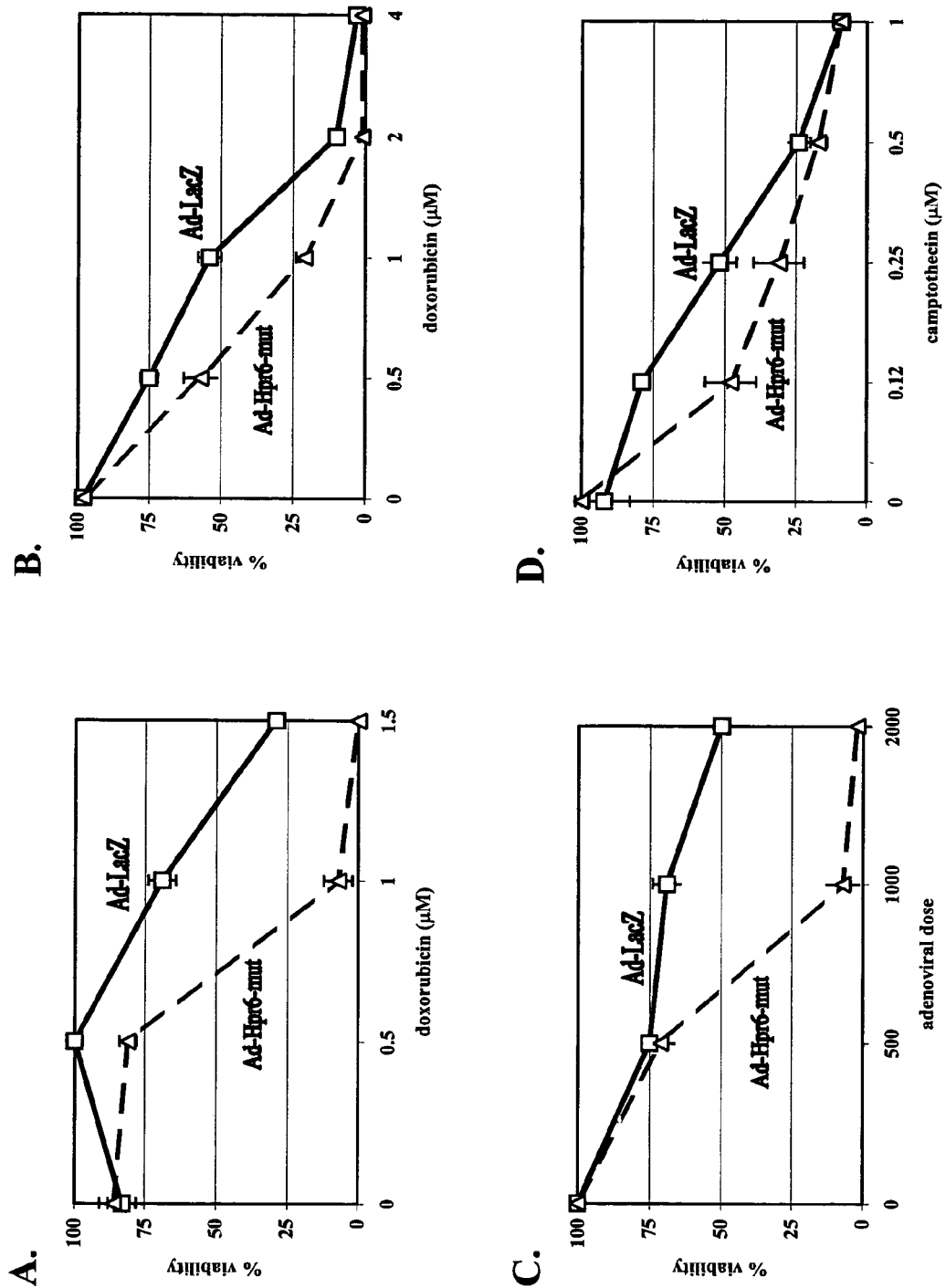
FIG. 3. Ad-Hpr6-mut acts synergistically with doxorubicin to induce cell death. 3A: graph showing viability of MDA-MB-231 cells infected either Ad-LacZ (solid line) or Ad-Hpr6-mut (dashed line), combined with increasing concentrations of doxorubicin (X axis). Viability was measured by MTT assay. 3B: graph showing viability of MDA-MB- 231 cells infected either Ad-LacZ (solid line) or Ad-Hpr6-mut (dashed line), combined with 0-41 µM doxorubicin (X axis). Viability was measured by trypan blue assay. 3C: graph showing viability of MDA-MB-231 cells treated with 1 µM doxorubicin combined with increasing doses of either Ad-LacZ (solid line) or Ad-Hpr6-mut (dashed line). Viability was measured by MTT assay. D, graph showing viability of MDA-MB-231 cells infected either Ad-LacZ (solid line) or Ad-Hpr6-mut (dashed line), combined with increasing concentrations of camptothecin (X axis). For all of the assays, error bars represent the standard deviations of triplicate measurements and the results shown are representative of at least three independent experiments.

Ad-Hpr6-mut infection triggered cell death in MDA-MB-231 cells following doxorubicin treatment (FIG. 3). Doxorubicin treatment caused significantly greater lethality in Ad-Hpr6-mut-infected cells (FIG. 3A-D, dashed lines) compared to cells infected with a control Ad-LacZ adenovirus (FIG. 3A-D, solid lines), and loss of viability increased proportionally with doxorubicin dose (FIG. 3A). Loss of viability was highly significant at a dose of 0.5 (100% viability for Ad-LacZ compared to 81% for Ad-Hpr6-mut, P=0.0003), 1 (Ad-LacZ, 69% compared to Ad-Hpr6-mut, 7%; P=0.0002), and 1.5 µM doxorubicin (Ad-LacZ, 29% viability compared to 0% for Ad-Hpr6-mut; P=0.008). In the absence of doxorubicin, the Ad-Hpr6-mut adenovirus had no detectable effect on tumor cell survival or proliferation (FIG. 3A-C, 0 dose of doxorubicin). Viability was also measured by trypan blue assay, and as expected, Ad-Hpr6-mut-infected cells were more sensitive to doxorubicin than Ad-LacZ-infected cells (FIG. 3B, 1 µM dose of doxorubicin, P=0.0006).

Doxorubicin-mediated cell death was dependent on the dose of the Ad-Hpr6-mut adenovirus (FIG. 3C). At a fixed dose of 1 µM doxorubicin, increased concentrations of the Ad-Hpr6-mut adenovirus increased cell death. There was no significant loss of viability at a dose of 500 pfu/cell, but loss of viability was highly significant at a dose of 1000 (70% viability for Ad-LacZ compared to 7% for Ad-Hpr6-mut, P=0.0002), and 2000 (50% viability for Ad-LacZ compared to 2% for Ad-Hpr6-mut, P=0.0001) pfu/cell Ad-Hpr6-mut. Thus, Hpr6 is a mediator of resistance to doxorubicin in MDA-MB-231 breast cancer cells.

A number of chemotherapeutic drugs target topoisomerases. The ability of Ad-Hpr6-mut to regulate survival following treatment with the drugs etoposide and camptothecin was tested. MDA-MB-231 cells were infected with Ad-LacZ or Ad-Hpr6-mut and treated with 125-1000 nM camptothecin, a topoisomerase I inhibitor. Synergism between Ad-Hpr6-mut and camptothecin was significant at 125 nM (FIG. 3D, 79%±9 for Ad-LacZ vs. 48%±2 for Ad-Hpr6-mut, P=0.005). We also detected a less dramatic but significant synergism between Ad-Hpr6-mut and etoposide. Ad-Hpr6-mut caused a significant increase in cell death at doses of 10 µM etoposide (27%±0.8 for Ad-LacZ vs. 20%±2 for Ad-Hpr6-mut, P=0.009). Thus, Hpr6-mut sensitizes breast cancer cells to multiple topoisomerase inhibitors.

Figure 4:
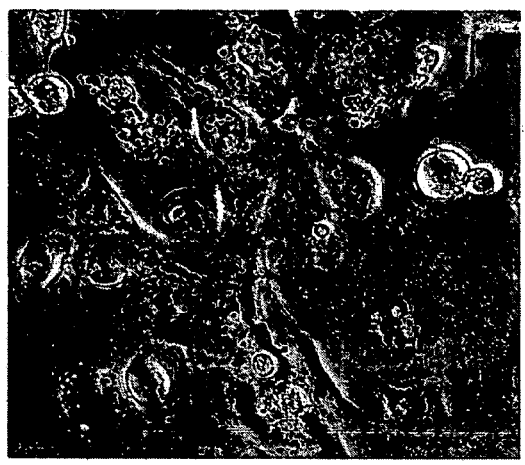
FIG. 4. Hpr6-mut induces cell death, but does not alter doxorubicin localization. 4A: Morphology of MDA-MB-231 cells infected with Ad-LacZ (left panel) or Ad-Hpr6-mut (right panel) and treated with 1 µM doxorubicin for 72 hours. Ad-Hpr6-mut-infected, doxorubicin-treated cells generally had a rounded or necrotic morphology. 4B: Hpr6-mut does not alter the localization or short-term accumulation of doxorubicin. MDA-MB-231 cells were infected with either Ad-LacZ (left panels) or Ad-Hpr6-mut (right panels) and treated with 10 µM doxorubicin for 1 hour. Cells were then fixed and visualized using bright-field microscopy (top panels) or fluorescence (bottom panels). In both groups of infected cells, doxorubicin accumulated in the nucleus to similar extents. These results were confirmed by F ACS analysis (data not shown).
Figure 4:
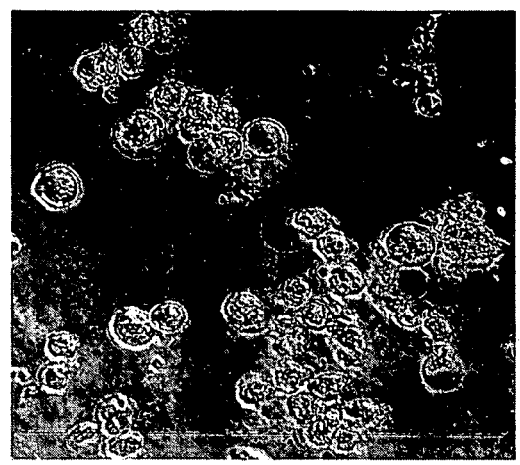
Figure 4:
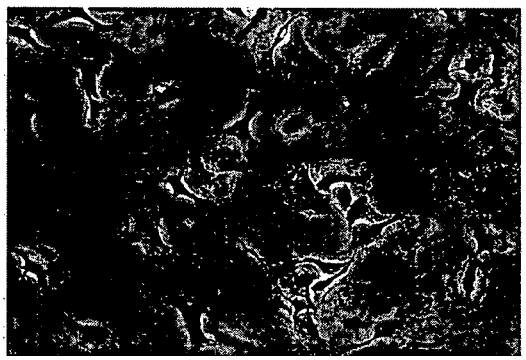
Figure 4:
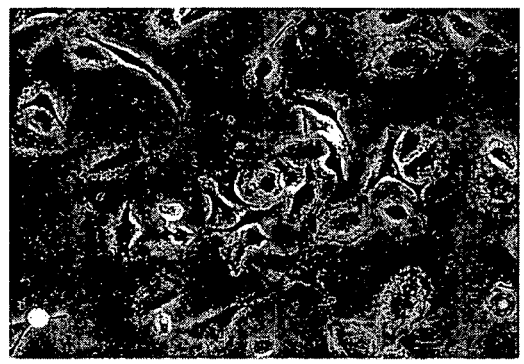
Figure 4:
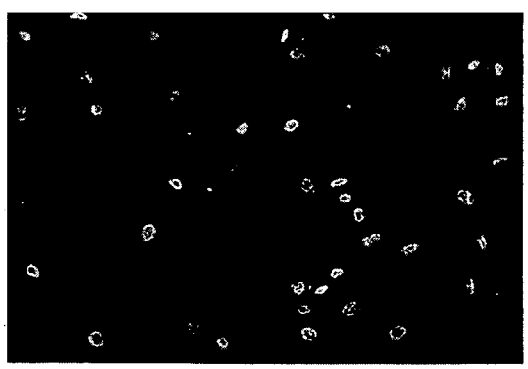
Figure 4:
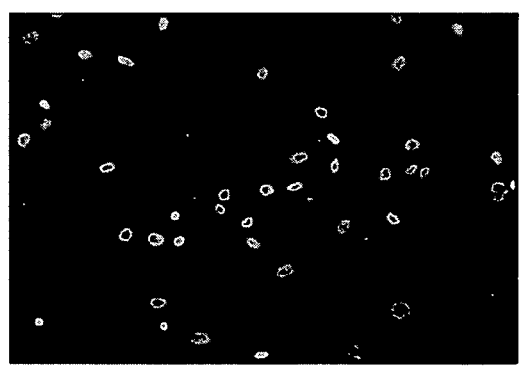

Doxorubicin frequently induces cell death via the apoptotic pathway. We detected rounded cells in MDA-MB-231 cells infected with Ad-Hpr6-mut and treated with doxorubicin, although the majority of the cells had a wasted, necrotic morphology (FIG. 4A, right panel). These cells were less evident in cells infected with a control adenovirus (FIG. 4A, left panel). In spite of the fact the cells were rounded, we were unable to detect classical markers of apoptosis, including cleavage of PARP, the focal adhesion kinase (F AK), endonucleolytic cleavage of chromosomal DNA, or nuclear condensation. We conclude that Hpr6-mut infection induces necrotic cell death in cells treated with doxorubicin.

EXAMPLE 6

Ad-Hpr6-mut infection does not cause cell death from peroxide or other chemotherapeutic drugs. Doxorubicin causes toxicity through the creation of reactive oxygen species and by inhibiting topoisomerase activity. We tested whether Ad-Hpr6-mut infection altered the response of MDA-MB-231 cells to oxidative damage. Cells treated with 25-100 µM hydrogen peroxide for 72 hours died to the same extent when infected with Ad-LacZ or Ad-Hpr6-mut (data not shown). We also tested the extent to which Ad-Hpr6-mut sensitized MDA-MB-23 I cells to additional chemotherapeutic drugs. MDA-MB-231 cells were infected with Ad-LacZ or Ad-Hpr6-mut and treated with the alkylating agent mechlorethamine, and Hpr6-mut expression had no effect on viability, (data not shown). Similar results were obtained with cisplatinum (data not shown). We conclude that the effects of Ad-Hpr6-mut are relatively specific and do not include all classes of damaging agents and drugs.

Because doxorubicin induces resistance through activation of multidrug transporters, it was believed possible that Hpr6 could act as a membrane-associated drug transport protein. To test this possibility, we infected MDA-MB-231 cells with Ad-LacZ or Ad-Hpr6-mut, then treated them with doxorubicin and examined doxorubicin accumulation by fluorescent microscopy 2 hours later. This approach has been previously used to examine the effect of P-glycoprotein on doxorubicin accumulation in breast cancer cells (Wu H et al. *Cancer Research* 2003; 63: 1515-9). The cellular morphologies of Ad-LacZ- and Ad-Hpr6-mut-infected cells were similar (FIG. 4B, upper panels), no difference in doxorubicin accumulation in Ad-LacZ vs. Ad-Hpr6-mut-infected cells was detected (FIG. 4B, bottom panels). Doxorubicin concentrations were also measured after 24 hours of treatment by fluorescence-activated cell sorting (F ACS) and no differences in doxorubicin levels were detected (data not shown). This result was consistent with the finding that Ad-Hpr6-mut does not synergize with mechlorethamine, because membrane drug transporters usually act on multiple drugs. In addition, we subsequently found that Hpr6 does not localize to the cell membrane (see Example 7). Thus, Hpr6 is unlikely to function as a membrane-associated multi drug transport protein.

EXAMPLE 7

Hpr6 is over-expressed in breast tumors.

Cell lines, culturing, and infection. MDA-MB-23 I human breast cancer cells were a kind gift from Dr. Carolyn Sartor (University of North Carolina at Chapel Hill) and were maintained in Dulbecco's Modified Eagle Medium with 10% Serum Supreme (Fisher, Chicago, Ill.) and penicillin and streptomycin at 37° C. in 5% CO2 in air. MCF-7 cells engineered to over-express Hpr6 have been described previously (Hand et al. *Journal of Cellular Biochemistry* 2003; 90: 534-47, incorporated herein in its entirety), and MCF-7 cells were maintained in Minimal Essential Medium containing 10% fetal bovine serum and antibiotics.

Figure 5:
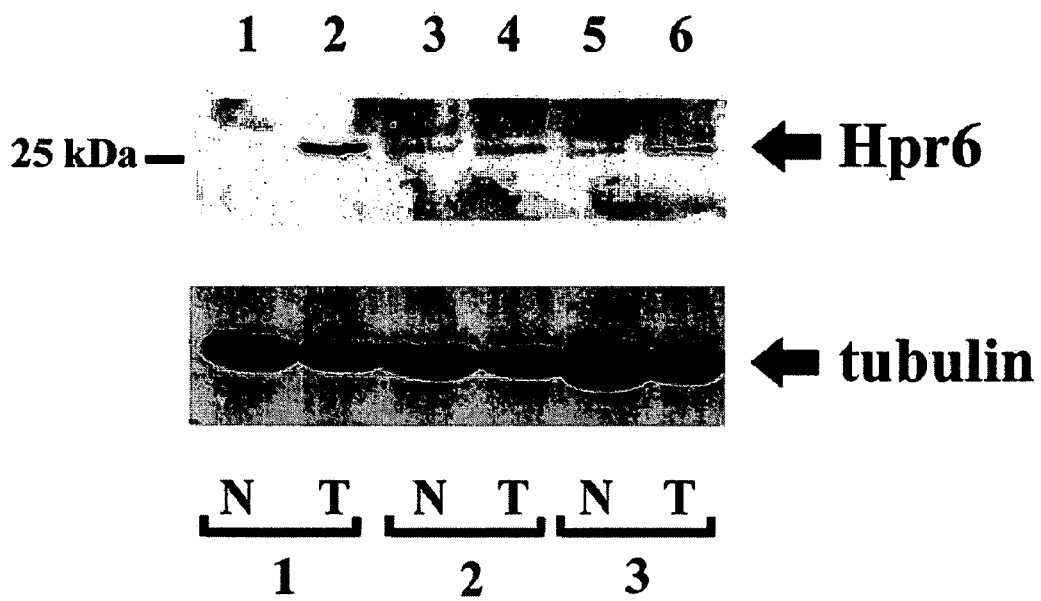
FIG. 5. Hpr6 overexpression in clinical breast tumor samples. 5A: western blot analysis of Hpr6 expression in paired normal (N, odd lanes) and tumor (T, even lanes) samples from the same patients (lanes 1-6). Hpr6 was overexpressed in tumors from patients 1 and 3. B, Hpr6 overexpression in unmatched breast tumor samples. Hpr6 expression was high in tumors from 4 separate patients (lanes 1, 3, 5, and 6).
Figure 5:
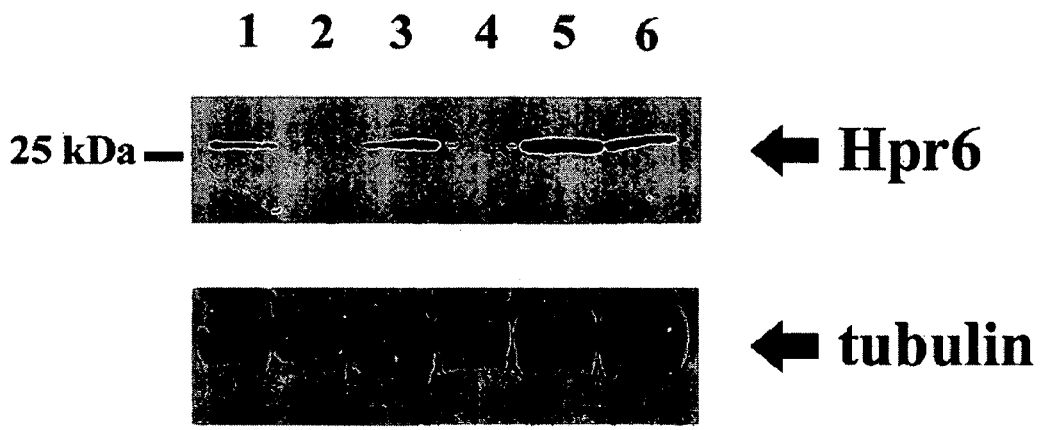

Because of the role of Hpr6 in chemotherapeutic resistance, the expression of Hpr6 in clinical breast tumor samples was analyzed. Hpr6 expression was determined in pairs of non-malignant breast tissue and adjacent breast tumors from the same patients. Hpr6 was expressed weakly in 9 separate non-malignant breast tissue samples (3 are shown in FIG. 5A, lanes 1, 3, and 5) and was over-expressed in tumors from 7 of these patients (FIG. 5A, examples in lanes 2 and 6). Hpr6 over-expression in tumors ranged from strong (FIG. 5A, lane 2) to moderate (FIG. 5A, lane 6), and Hpr6 was not over-expressed in some tumors (FIG. 5A, lane 4). Hpr6 was also highly expressed in 4/11 non-matched breast tumor samples (FIG. 5B). Taking all of the samples together, it was found that Hpr6 was highly expressed in 6/18 breast tumors and was moderately expressed in 5/18 tumors (FIG. 5C, right). Low expression levels ere found in 6/18 breast tumors, and a single tumor had no detectable expression of Hpr6 (FIG. 5C, right). In all cases, non-malignant breast tissues exhibited weak but detectable expression of Hpr6 (FIG. 5C, left). Thus, Hpr6 is over-expressed in breast cancer.

Figure 6:
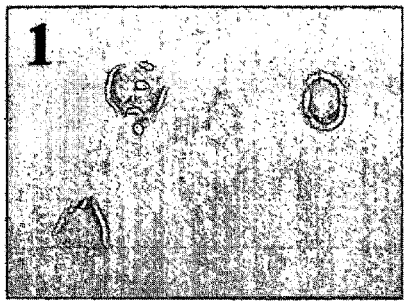
FIG. 6. Hpr6 localizes to the perinuclear region in MCF-7 breast cancer cells. MCF-7 cells were transfected with the control plasmid pBK-CMV (panels 1 and 2) or the Hpr6 expression plasmid pBK-Hpr6 (panels 3-6) and isolates were selected that stably expressed Hpr6 (ref. 13). Cells were plated on 4-well chamber slides and analyzed by bright field microscopy (panels 1, 3, and 5) or by immunofluorescence after staining with an antibody directed to HA (panels 2, 4, and 6). Panels 1-4are at 100× resolution, while panels 5 and 6 are at 400×.
Figure 6:
Figure 6:
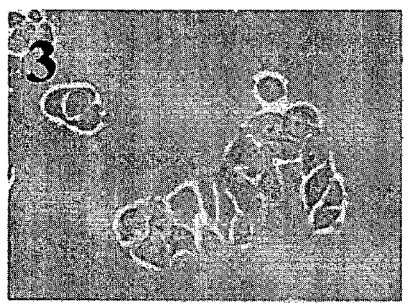
Figure 6:
Figure 6:
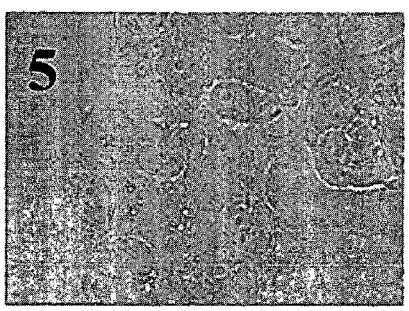
Figure 6:
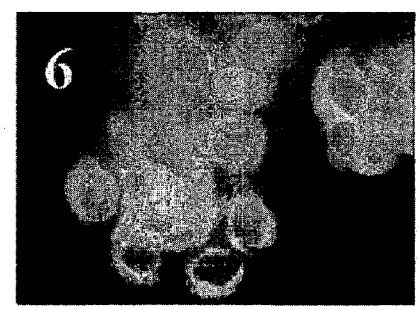

The sub-cellular localization of Hpr6 was determined. The antibody used for western blotting was raised to a peptide sequence at the Hpr6 amino terminus, and no staining was detected with this antibody (data not shown). MCF-7 breast cancer cells expressing an epitope-tagged Hpr6 were stained with a monoclonal antibody to the epitope tag by immunofluorescence. No staining was detectable in MCF-7 cells harboring a control plasmid (FIG. 6, panel 2), while the majority of MCF-7/Hpr6 cells exhibited sharp perinuclear staining (FIG. 6, panels 4 and 6). This perinuclear staining resembled that of the endoplasmic reticulum dye BODIPY Brefeldin A (Hand and Craven, unpublished observations), suggesting that Hpr6 localizes to the endoplasmic reticulum.

What is claimed is:

1. An isolated polypeptide having the amino acid sequence of SEQ ID NO:11.

\* \* \* \* \*

SEQUENCE LISTING

<160> NUMBER OF SEQ ID NOS: 10

<210> SEQ ID NO 1
<211> LENGTH: 195
<212> TYPE: PRT
<213> ORGANISM: Homo sapiens

<400> SEQUENCE: 1

```
Met Ala Ala Glu Asp Val Val Ala Thr Gly Ala Asp Pro Ser Asp Leu
1               5                   10                  15

Glu Ser Gly Gly Leu Leu His Glu Ile Phe Thr Ser Pro Leu Asn Leu
            20                  25                  30

Leu Leu Leu Gly Leu Cys Ile Phe Leu Leu Tyr Lys Ile Val Arg Gly
        35                  40                  45

Asp Gln Pro Ala Ala Ser Gly Asp Ser Asp Asp Glu Pro Pro Pro
    50                  55                  60

Leu Pro Arg Leu Lys Arg Arg Asp Phe Thr Pro Ala Glu Leu Arg Arg
65                  70                  75                  80

Phe Asp Gly Val Gln Asp Pro Arg Ile Leu Met Ala Ile Asn Gly Lys
                85                  90                  95

Val Phe Asp Val Thr Lys Gly Arg Lys Phe Tyr Gly Pro Glu Gly Pro
            100                 105                 110

Tyr Gly Val Phe Ala Gly Arg Asp Ala Ser Arg Gly Leu Ala Thr Phe
        115                 120                 125

Cys Leu Asp Lys Glu Ala Leu Lys Asp Glu Tyr Asp Asp Leu Ser Asp
    130                 135                 140

Leu Thr Ala Ala Gln Gln Glu Thr Leu Ser Asp Trp Glu Ser Gln Phe
145                 150                 155                 160

Thr Phe Lys Tyr His His Val Gly Lys Leu Leu Lys Glu Gly Glu Glu
                165                 170                 175

Pro Thr Val Tyr Ser Asp Glu Glu Pro Lys Asp Glu Ser Ala Arg
            180                 185                 190

Lys Asn Asp
        195
```

<210> SEQ ID NO 2
<211> LENGTH: 619
<212> TYPE: DNA
<213> ORGANISM: Homo sapiens

<400> SEQUENCE: 2

```
atggctgccg aggatgtggt ggcgactggc gccgacccaa gcgatctgga gagcggcggg      60
ctgctgcatg agatttttcac gtcgccgctc aacctgctgc tgcttggcct ctgcatcttc     120
ctgctctaca agatcgtgcg cggggaccag ccggcggcca gcggcgacag cgacgacgac    180
gagccgcccc ctctgccccg cctcaagcgg cgcgacttca ccccgccga gctgcggcgc      240
```

```
ttcgacggcg tccaggaccc gcgcatactc atggccatca acggcaaggt gttcgatgtg      300
accaaaggcc gcaaattcta cgggcccgag gggccgtatg gggtctttgc tggaagagat      360
gcatccaggg gccttgccac attttgcctg gataaggaag cactgaagga tgagtacgat      420
gacctttctg acctcactgc tgcccagcag gagactctga gtgactggga gtctcagttc      480
actttcaagt atcatcacgt gggcaaactg ctgaaggagg gggaggagcc cactgtgtac      540
tcagatgagg aagaaccaaa agatgagagt gcccggaaaa atgattaaag cattcagtgg      600
aagtatatct attttgta                                                    619
```

```
<210> SEQ ID NO 3
<211> LENGTH: 99
<212> TYPE: PRT
<213> ORGANISM: Homo sapiens

<400> SEQUENCE: 3

Phe Thr Pro Ala Glu Leu Arg Arg Phe Asp Gly Val Gln Asp Pro Arg
1               5                   10                  15

Ile Leu Met Ala Ile Asn Gly Lys Val Phe Asp Val Thr Lys Gly Arg
            20                  25                  30

Lys Phe Tyr Gly Pro Glu Gly Pro Tyr Gly Val Phe Ala Gly Arg Asp
        35                  40                  45

Ala Ser Arg Gly Leu Ala Thr Phe Cys Leu Asp Lys Glu Ala Leu Lys
    50                  55                  60

Asp Glu Tyr Asp Asp Leu Ser Asp Leu Thr Ala Ala Gln Gln Glu Thr
65                  70                  75                  80

Leu Ser Asp Trp Glu Ser Gln Phe Thr Phe Lys Tyr His His Val Gly
                85                  90                  95

Lys Leu Leu

<210> SEQ ID NO 4
<211> LENGTH: 12
<212> TYPE: PRT
<213> ORGANISM: Artificial Sequence
<220> FEATURE:
<223> OTHER INFORMATION: Chemically Synthesized

<400> SEQUENCE: 4

Asp Tyr Pro Tyr Asp Val Pro Asp Tyr Ala Glu Ser
1               5                   10

<210> SEQ ID NO 5
<211> LENGTH: 21
<212> TYPE: PRT
<213> ORGANISM: Homo sapiens
<220> FEATURE:
<221> NAME/KEY: MISC_FEATURE
<222> LOCATION: (5)..(5)
<223> OTHER INFORMATION: X = any other amino acid
<220> FEATURE:
<221> NAME/KEY: MISC_FEATURE
<222> LOCATION: (9)..(10)
<223> OTHER INFORMATION: X = any other amino acid
<220> FEATURE:
<221> NAME/KEY: MISC_FEATURE
<222> LOCATION: (14)..(14)
<223> OTHER INFORMATION: X = any other amino acid
<220> FEATURE:
<221> NAME/KEY: MISC_FEATURE
<222> LOCATION: (19)..(19)
<223> OTHER INFORMATION: X = any other amino acid

<400> SEQUENCE: 5
```

```
Phe Tyr Gly Pro Xaa Gly Pro Tyr Xaa Xaa Phe Ala Gly Xaa Asp Ala
1               5                   10                  15

Ser Arg Xaa Leu Ala
            20

<210> SEQ ID NO 6
<211> LENGTH: 90
<212> TYPE: DNA
<213> ORGANISM: Artificial Sequence
<220> FEATURE:
<223> OTHER INFORMATION: Chemically Synthesized

<400> SEQUENCE: 6
cccgggggat ccgacgccgc caccatggaa tccgactacc cctatgatgt gcccgattac      60
gtcgagtccg tcgccgagga tgtggtggcg                                      90

<210> SEQ ID NO 7
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 7
cccatacggc ccctcgggcc                                                 20

<210> SEQ ID NO 8
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 8
acaagatcgt gcgcgggga                                                  19

<210> SEQ ID NO 9
<211> LENGTH: 34
<212> TYPE: DNA
<213> ORGANISM: Artificial Sequence
<220> FEATURE:
<223> OTHER INFORMATION: Chemically Synthesized

<400> SEQUENCE: 9
tgtgggcccc tcgagaaact tatagcaagt gctc                                 34

<210> SEQ ID NO 10
<211> LENGTH: 59
<212> TYPE: DNA
<213> ORGANISM: Artificial Sequence
<220> FEATURE:
<223> OTHER INFORMATION: Chemically Synthesized

<400> SEQUENCE: 10
tacgggcccg aggggccgta tgggtctttt gctggaagag atgcatccag gggccttgc      59
```